(12) United States Patent
Srinivasa Naidu et al.

(10) Patent No.: US 11,992,369 B2
(45) Date of Patent: *May 28, 2024

(54) INTELLIGENT ULTRASOUND SYSTEM FOR DETECTING IMAGE ARTEFACTS (71) Applicant: KONINKLIJKE PHILIPS N.V., Eindhoven (NL)

(72) Inventors: Raghavendra Srinivasa Naidu, Auburndale, MA (US); Man Nguyen, Melrose, MA (US); Christine Menking Swisher, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 302 days.

This patent is subject to a terminal disclaimer.

(21) Appl. No.: 16/760,962

(22) PCT Filed: Oct. 29, 2018

(86) PCT No.: PCT/EP2018/079529
§ 371 (c)(1),
(2) Date: May 1, 2020

(87) PCT Pub. No.: WO2019/086365
PCT Pub. Date: May 9, 2019

(65) Prior Publication Data
US 2020/0297318 A1  Sep. 24, 2020

Related U.S. Application Data

(60) Provisional application No. 62/580,635, filed on Nov. 2, 2017.

(51) Int. Cl.
*A61B 8/00* (2006.01)
*A61B 8/08* (2006.01)
*G06N 3/02* (2006.01)

(52) U.S. Cl.
CPC .......... *A61B 8/465* (2013.01); *A61B 8/5215* (2013.01); *A61B 8/5269* (2013.01); *G06N 3/02* (2013.01)

(58) Field of Classification Search
None
See application file for complete search history.

(56) References Cited

U.S. PATENT DOCUMENTS

2009/0088639 A1 * 4/2009 Maschke .................. B25J 11/00
600/443
2010/0305441 A1 12/2010 Lin et al.
(Continued)

FOREIGN PATENT DOCUMENTS

| RU | 2237965 C2 | 10/2004 |
| WO | 2016036516 A1 | 3/2016 |
| WO | 2017156329 A1 | 9/2017 |

OTHER PUBLICATIONS

Kumar et al: "Understanding Anatomy Classification Through Attentive Response Maps"; 2018 IEEE 15th International Symposium on Biomedical Imaging (ISBI 2018), 4 Page Document.
(Continued)

Primary Examiner — Katherine L Fernandez
Assistant Examiner — Farouk A Bruce (57) ABSTRACT

The present disclosure describes ultrasound imaging systems and methods configured to identify and remove image artefacts from ultrasound image frames by applying a neural network to the frames. Systems may include an ultrasound transducer configured to acquire echo signals responsive to ultrasound pulses transmitted toward a target region. One or more processors communicatively coupled with the ultrasound transducer may be configured to generate an image frame from the ultrasound echoes and apply a neural network to the image frame. The neural network determines whether an artefact is present in the image frame, and
(Continued)

identifies the type of artefact detected. The processors can also generate an indicator conveying the presence of the artefact, which can be displayed on a user interface. The processors can further generate an instruction for adjusting the ultrasound transducer based on the presence and type of artefact present within the image frame.

18 Claims, 8 Drawing Sheets

(56) References Cited

U.S. PATENT DOCUMENTS

| | | | |
|---|---|---|---|
| 2014/0221832 A1 | 8/2014 | El-Zehiry et al. | |
| 2014/0321760 A1* | 10/2014 | Oishi | A61B 5/7203 |
| | | | 382/218 |
| 2016/0157831 A1* | 6/2016 | Kang | A61B 8/5276 |
| | | | 600/443 |
| 2016/0317118 A1 | 11/2016 | Parthasarathy et al. | |
| 2016/0350620 A1* | 12/2016 | Rao | A61B 8/0891 |
| 2017/0143312 A1 | 5/2017 | Hedlund et al. | |
| 2017/0360412 A1* | 12/2017 | Rothberg | G06T 19/006 |
| 2018/0177461 A1* | 6/2018 | Bell | A61B 5/7425 |
| 2018/0260665 A1* | 9/2018 | Zhang | G06F 18/22 |
| 2019/0107612 A1* | 4/2019 | Holl | G01S 7/5205 |

OTHER PUBLICATIONS

PCT/EP2018/079529 ISR and Written Opinion, dated Feb. 25, 2019, 13 Pages.

* cited by examiner

INTELLIGENT ULTRASOUND SYSTEM FOR DETECTING IMAGE ARTEFACTS

CROSS-REFERENCE TO PRIOR APPLICATIONS

This application is the U.S. National Phase application under 35 U.S.C. § 371 of International Application No. PCT/EP2018/079529, filed on Oct. 29, 2018, which claims the benefit of U.S. Provisional Patent Application No. 62/580,635, filed on Nov. 2, 2017. These applications are hereby incorporated by reference herein.

TECHNICAL FIELD

The present disclosure pertains to ultrasound systems and methods for identifying artifacts in ultrasound images using a neural network. Particular implementations involve systems configured to identify artifacts during ultrasound imaging and provide instructions for adjusting an ultrasound probe to remove the artifacts from acquired ultrasound images.

BACKGROUND

Ultrasound images may contain various artifacts that obscure the bodily features captured in the images. For example, image artifacts commonly appear in ultrasound images as a result of ultrasound physics and operator interference. Inconsistent echogenicity between different features can produce shadowing effects, specifically, while variation in tissue sound speeds and reflection of high-contrast tissue impedance can result in mirror images and reverberations. The appearance of such artifacts can impede an operator's ability to accurately interpret the features within the ultrasound images, which may lead to incorrect diagnoses. The image artifacts can also interfere with ultrasound-guided interventional procedures.

Removing artifacts from ultrasound images can often be accomplished by adjusting the position, orientation, and/or operational settings of an ultrasound transducer used to acquire the images. However, inexperienced ultrasound operators may not recognize artifacts appearing within the images, or may not know the adjustments necessary to make the artifacts disappear. Accordingly, ultrasound imaging systems capable of recognizing image artifacts and the steps that may be taken to remove the artifacts may be desirable.

SUMMARY

The present disclosure describes systems and methods for improving the quality and interpretation of ultrasound images by identifying and removing artifacts obscuring the features included in the images. The systems may be used by novice ultrasound users unable to reliably identify artifacts and/or adjust an ultrasound transducer in the manner necessary to remove them. By reducing operational error, the systems disclosed herein can improve the quality of ultrasound images acquired during a scan and the diagnoses made based on such images. Systems may implement a neural network trained to detect the presence of various artifacts that may appear during an ultrasound scan. In addition to detecting the presence of the artifacts, the systems can determine the type of each artifact. Artifact types may include reverberations, shadows, or mirror images, for example. The neural network may be further trained to output an instruction or corrective action for adjusting an ultrasound transducer and/or settings thereof in the manner necessary to remove the artifact(s) from the images. The instruction may vary based on the type of artifact identified, such that an instruction for removing a reverberation artifact may be different than an instruction for removing a mirror image artifact. In some examples, the instruction is provided to a user operating the ultrasound equipment. In other examples, the instruction is transmitted to a system component, e.g., a controller, which is configured to automatically adjust the ultrasound transducer in accordance with the instruction, thereby removing the artifact(s) without user intervention.

In accordance with some examples, an ultrasound imaging system may include an ultrasound transducer configured to acquire echo signals responsive to ultrasound pulses transmitted toward a target region. One or more processors in communication with the ultrasound transducer may also be included. The processors may be configured to generate at least one image frame from the ultrasound echoes; apply a neural network to the image frame, in which the neural network determines a presence and type of an artifact in the image frame; generate an indicator based on the determined presence of the artifact; cause the indicator to be displayed on a user interface in communication with the processors; and generate an instruction for adjusting the ultrasound transducer based on the determined presence and type of the artifact.

In some examples, the processors may be further configured to transmit the instruction to a controller communicatively coupled with the ultrasound transducer. In some embodiments, the controller may be configured to adjust the ultrasound transducer by modifying an operating parameter thereof based on the instruction received from the processors. In some examples, the operating parameter may include a position, an orientation, a focal depth, a beam angle, an imaging modality, or a frequency of the ultrasound transducer. In some embodiments, the ultrasound transducer may be physically coupled with a robotic arm configured to move the ultrasound transducer.

In some examples, the processors may be further configured to generate and cause to be displayed an ultrasound image from the image frame on the user interface. In some embodiments, the indicator may include a graphic overlay or position marker superimposed on the ultrasound image displayed on the user interface. In some examples, the artifact may include a reverberation, an acoustic shadow, an acoustic enhancement, a mirror image, or an edge shadow. In some embodiments, the neural network may include a plurality of neural network models, each of the neural network models associated with one of a plurality of preset imaging modalities selectable by a user. In some examples, each of the preset imaging modalities may be configured to cause the ultrasound transducer to acquire echo signals from a distinct target region by implementing a set of operating parameters specific to the distinct target region. In some embodiments, the one or more processors may be configured to generate and cause to be displayed a predicted artifact-free ultrasound image. In some embodiments, the instruction may be displayed on the user interface. In some examples, following the instruction causes the artifact to be removed from the image frame. In some embodiments, the neural network may be operatively associated with a training algorithm configured to receive an array of training inputs and known outputs, wherein the training inputs comprise ultrasound image frames containing artifacts, and the known outputs comprise an operational parameter adjustment configured to remove the artifacts form the ultrasound image frames. In some examples, the neural network may include a plurality of neural network models, each of the neural network models associated with one of a plurality of subsets of training inputs, each of the subsets associated with one of a plurality of preset imaging modalities selectable by a user.

In accordance with some examples, a method of ultrasound imaging may involve acquiring echo signals responsive to ultrasound pulses transmitted into a target region by a transducer operatively coupled to an ultrasound system; generating at least one image frame from the ultrasound echoes; applying a neural network to the image frame, in which the neural network determines a presence and type of an artifact in the image frame; generating an indicator based on the determined presence of the artifact; displaying the indicator on a user interface; and generating an instruction for adjusting the transducer based on the determined presence and type of the artifact, the instruction comprising an operational guidance for removing the artifact from the image frame.

In some examples, the method may further involve selecting an imaging modality for acquiring echo signals, the imaging modality comprising operational parameters specific to the target region. In some embodiments, the method may further involve transmitting the instruction to a controller communicatively coupled with the transducer. In some examples, the method may further involve modifying an operating parameter of the transducer based on the instruction. In some embodiments, the method may further involve displaying the instruction on the user interface. In some examples, the method may further involve training the neural network using ultrasound images frames containing a plurality of different artifacts and expert instructions for adjusting the transducer based on the plurality of different artifacts. In some examples, the method may further involve generating a predicted ultrasound image without the artifact.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

An ultrasound system according to the present disclosure may utilize a neural network, for example a deep neural network (DNN), a convolutional neural network (CNN) or the like, to identify various image artifacts, e.g., reverberations, which may appear during ultrasound imaging. In some examples, the neural network may be trained using any of a variety of currently known or later developed machine learning techniques to obtain a neural network (e.g., a machine-trained algorithm or hardware-based system of nodes) that are able to analyze input data in the form of ultrasound image frames and identify certain features, including one or more image artifacts. Neural networks may provide an advantage over traditional forms of computer programming algorithms in that they can be generalized and trained to recognize data set features by analyzing data set samples rather than by reliance on specialized computer code. By presenting appropriate input and output data to a neural network training algorithm, the neural network of an ultrasound system according to the present disclosure can be trained to identify artifacts and provide instructions for adjusting an ultrasound transducer in a manner that results in removal of the artifacts from ultrasound images. In some examples, the instructions can be transmitted to a controller configured to automatically adjust an ultrasound transducer according to the instructions, without user intervention. Additionally or alternatively, the instructions may be translated to one or more image processing operations for removing the artifacts from the ultrasound image.

An ultrasound system in accordance with principles of the present invention may include or be operatively coupled to an ultrasound transducer configured to transmit ultrasound pulses toward a medium, e.g., a human body or specific portions thereof, and generate echo signals responsive to the ultrasound pulses. The ultrasound system may include a beamformer configured to perform transmit and/or receive beamforming, and a display configured to display, in some examples, ultrasound images generated by the ultrasound imaging system. The ultrasound imaging system may include one or more processors and at least one model of a neural network, which may be implemented in hardware and/or software components. The neural network can be machine trained to identify one or more image artifacts, such as reverberations or mirror images, and output an indication of the presence and/or type of such artifacts.

The neural network implemented according to the present disclosure may be hardware—(e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a machine-trained algorithm for identifying various artifacts within ultrasound images and, in some examples, output an indication of the presence, absence, and/or type thereof. The ultrasound system may include a display or graphics processor, which is operable to arrange the ultrasound images and/or additional graphical information, which may include annotations, tissue information, patient information, indicators, and other graphical components, in a display window for display on a user interface of the ultrasound system. In some embodiments, the ultrasound images and tissue information, including information regarding the presence and/or type of artifacts, may be provided to a storage and/or memory device, such as a picture archiving and communication system (PACS) for reporting purposes or future machine training (e.g., to continue to enhance the performance of the neural network). In some examples, ultrasound images obtained during a scan may not be displayed to the user operating the ultrasound system, but may be analyzed by the system for the presence or absence of image artifacts as an ultrasound scan is performed.

Figure 1:
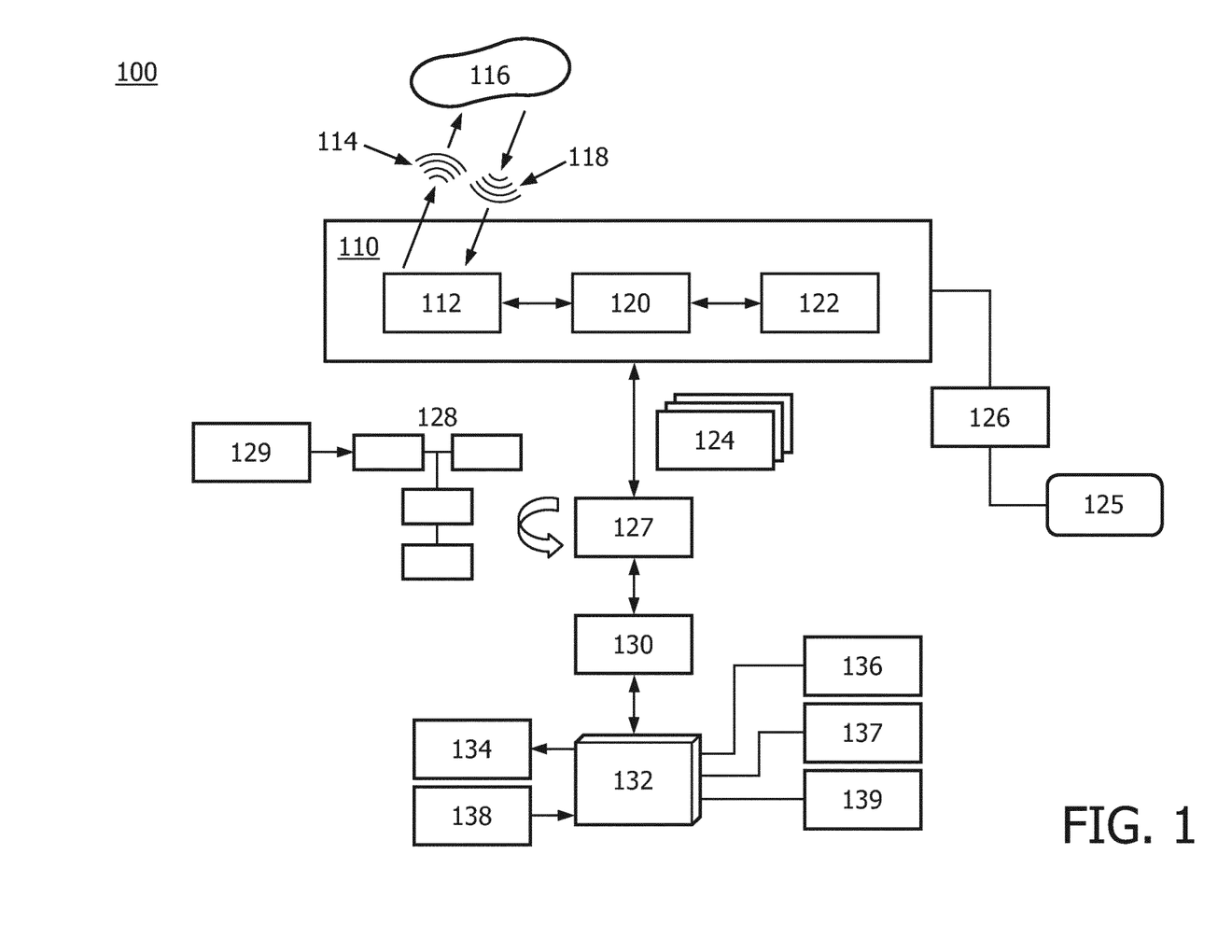
FIG. 1 is a block diagram of an ultrasound system in accordance with principles of the present disclosure.

FIG. 1 shows an example ultrasound system according to principles of the present disclosure. The ultrasound system 100 may include an ultrasound data acquisition unit 110. The ultrasound data acquisition unit 110 may include an ultrasound transducer or probe which includes an ultrasound sensor array 112 configured to transmit ultrasound pulses 114 into a target region 116 of a subject, e.g., abdomen, and receive echoes 118 responsive to the transmitted pulses. As further shown, the ultrasound data acquisition unit 110 may include a beamformer 120 and a signal processor 122, which may be configured to generate a plurality of discrete ultrasound image frames 124 from the ultrasound echoes 118 received at the array 112. In some embodiments, the system 100 may also include a controller 125 coupled with the ultrasound data acquisition unit 110. The controller 125 may be configured to adjust the position, orientation, and/or operational settings of the data acquisition unit 110 as part of an automatic feedback loop. A mechanical adjustment mechanism 126, such as a robotic arm, may be configured to physically maneuver the ultrasound data acquisition unit 110 at the direction of the controller 125. In some examples, the signal processor 122 may be housed with the sensor array 112 or it may be physically separate from but communicatively (e.g., via a wired or wireless connection) coupled thereto.

The system may also include an artifact detection engine 127, e.g., a computational module or circuitry (e.g., application specific integrated circuit (ASIC), configured to implement a neural network 128. The neural network 128 may be configured to receive the image frames 124 and determine a presence and/or type of an imaging artifact within each frame. To train the neural network 128, various types of training data 129 may be input into the network at various moments before and/or after applying the network. While only one neural network 128 is illustrated in FIG. 1 for clarity and simplicity of the illustration, a plurality of distinct neural network models may be associated or communicatively coupled with the artifact detection engine 127. Each model of the neural network 128 may be pre-trained via a training algorithm to determine a presence and/or type of imaging artifact in image frames 124 acquired during a specific imaging application. Accordingly, each model may be pre-trained with a distinct set of training data 129 obtained via imaging a distinct target region 116.

In some examples, the system 100 also includes a display processor 130 coupled with the artifact detection engine 127 and a user interface 132. In some examples, the display processor 130 may be configured to generate ultrasound images 134 from the image frames 124 and an indicator 136 that conveys the presence and/or type of image artifact(s) within each of the image frames 124. The user interface 132 may be configured to display the ultrasound images 134 of the region in real time as an ultrasound scan is being performed, along with the indicator 136. In some embodiments, the user interface 132 may not display ultrasound images, but may display the indicator 136, such that a user may not be able to see the bodily features and/or image artifacts shown in the image frames, but may display the indicator 136, such that a user will still be notified of their ultrasonic detection. The user interface 132 may also be configured to display one or more instructions 137 based on the detected presence and/or type of artifacts appearing within the image frames 124. The instructions 137 may include directions for adjusting the data acquisition unit 110 in a manner that removes the artifact(s) from the image frames 124, thereby improving the quality of the image frames. The user interface 132 may also be configured to receive a user input 138 at any time before, during, or after an ultrasound scan. In some examples, the user input 138 can include a preset imaging modality selection that specifies operational parameters for imaging particular bodily features, e.g., bladder, lungs, kidneys, etc. The operational parameters can include pre-specified focal depths, pulse frequencies, scan line numbers, scan line densities, or other settings. The particular model of the neural network 128 applied to the acquired image frames 124 may depend on the preset imaging modality selected by a user. For example, the neural network model 128 applied during cardiac imaging may be different than the neural network model applied when imaging the bladder or a kidney. Each model of the neural network 128 may thus be pre-trained to identify artifacts in specific types of image frames 124 acquired from a specific target region 116. Selection of a preset imaging modality invokes implementation of the correct model of the neural network 128.

The configuration of the system 100 shown in FIG. 1 may vary. As further shown, the user interface 132 can display predicted artifact-free image frames 139 generated by the neural network 128. For example, the system 100 can be portable or stationary. Various portable devices, e.g., laptops, tablets, smart phones, or the like, may be used to implement one or more functions of the system 100 at a location separate from a clinic, e.g., a remote point of care. In examples that incorporate such devices, the ultrasound sensor array 112 may be connectable via a USB interface, for example.

The ultrasound data acquisition unit 110 may be configured to acquire ultrasound data from one or more regions of interest, which may include various tissues, organs, or other internal bodily structures. The ultrasound sensor array 112 may include at least one transducer array configured to transmit and receive ultrasonic energy. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging. In addition to B-mode imaging, imaging modalities implemented according to the disclosures herein can also include shear-wave and/or Doppler, for example.

A variety of users may handle and operate the ultrasound data acquisition unit 110 to perform the methods described herein. In some examples, the user may include an inexperienced, novice ultrasound operator unable to consistently identify and/or remove artifacts from ultrasound images. The improved ultrasound technology disclosed herein enables such users to perform effective ultrasound imaging by identifying artifacts within acquired ultrasound image frames 124 and providing instructions to the users for adjusting an ultrasound transducer in a manner that removes the artifacts from the images. In examples where a mechanical adjustment mechanism 126 is used to control the position and/or orientation of the ultrasound transducer, the instructions for removing artifacts may be communicated to the controller 125 configured to cause the robotic equipment to make the necessary adjustments automatically, without user input. By identifying artifacts and providing precise instructions for removing the artifacts, the systems disclosed herein may lead to improved image interpretation and diagnosis.

As further shown in FIG. 1, the data acquisition unit 110 may also include a beamformer 120, e.g., comprising a microbeamformer or a combination of a microbeamformer and a main beamformer, coupled to the ultrasound sensor array 112. The beamformer 120 may control the transmission of ultrasonic energy, for example by forming ultrasonic pulses into focused beams. The beamformer 120 may also be configured to control the reception of ultrasound signals such that discernable image data may be produced and processed with the aid of other system components. The role of the beamformer 120 may vary in different ultrasound probe varieties. In some embodiments, the beamformer 120 may comprise two separate beamformers: a transmit beamformer configured to receive and process pulsed sequences of ultrasonic energy for transmission into a subject, and a separate receive beamformer configured to amplify, delay, and/or sum received ultrasound echo signals. In some embodiments, the beamformer 120 may comprise a microbeamformer operating on groups of sensor elements for both transmit and receive beamforming, coupled to a main beamformer which operates on the group inputs and outputs for both transmit and receive beamforming, respectively.

The signal processor 122 may be communicatively, operatively, and/or physically coupled with the sensor array 112 and/or the beamformer 120. In the example shown in FIG. 1, the signal processor 122 is included as an integral component of the data acquisition unit 110, but in other examples, the signal processor 122 may be a separate component. The signal processor 122 may be configured to receive unfiltered and disorganized ultrasound data embodying the ultrasound echoes 118 received at the sensor array 112. From this data, the signal processor 122 may continuously generate a plurality of ultrasound image frames 124 as a user scans the region 116.

The artifact detection engine 127 can receive image frames 124 from the data acquisition unit 110. The engine 127 may then prepare the received image data embodied in the image frames 124 for input into the neural network 128. In embodiments, the engine 127 may input image frames 124 into a particular model of the neural network 128 based on the preset imaging modality selected by the user. In some examples, preparing the data involves creating triplicate replications of the data such that various neural network models, e.g., Inception, Alexnet and/or Resnet, can be utilized to identify image artifacts and adjustment options for removing them. In specific embodiments, the triplicate replications can include three, 8-bit representations of the dynamic range, i.e., the high-signal, low dynamic range image; the low-signal, low dynamic range image; and the compressed high dynamic range image with adaptive histogram equalization.

In various embodiments, the neural network 128 may be embedded within or at least in communication with the signal processor 122 and/or the artifact detection engine 127. The neural network 128 may be configured to receive and input the ultrasound image frames 124 directly from the signal processor 122 in some examples, and determine whether one or more artifacts are present within each of the image frames 124. In some embodiments, the neural network 128 may be a convolutional neural network (CNN) comprised of variously organized neural layers and sublayers collectively trained to recognize various image artifacts within ultrasound image frames. The neural network 128 may include multiple neural network models, each model trained using a distinct set of training data 129 collected by imaging a particular target region 116 during implementation of a specific imaging modality. The neural network 128 may automatically detect the presence, absence, and/or type of artifacts within each received image frame 124, and may be implemented within two- or three-dimensional ultrasound imaging systems. The neural network 128 may also identify the type of each artifact detected within the image frames 124. Depending on the artifact type, the neural network 128 may be further configured to output an instruction 137 for removing the artifact from the images. In addition, the neural network 128 may be configured to generate predicted artifact-free image frames 139. The artifact-free image frames 139 can comprise the original image frames 124, but with the artifacts removed therefrom.

The display processor 130 communicatively coupled with the neural network 128 may be configured to generate an indicator 136 based on the determinations made by the neural network 128. In some implementations, the indicator 136 may indicate the presence, absence, and/or type of artifact within an image frame 124. Upon receiving the ultrasound images 124 and/or the indicator 136, the user interface 132 may then display the images and/or indicator. The indicator 136 may be displayed concurrently with, e.g., superimposed on top of or next to, the ultrasound images 134 in real time as the images are obtained. Accordingly, the indicator 136 may instantly notify the user of the presence or absence of one or more artifacts. In some examples, the indicator 136 may comprise a sensory cue that is not visibly displayed, such as a vibration of the ultrasound probe or an audible cue emitted from speakers coupled with the ultrasound system 100. The indicator 136 may also comprise a light that turns on and off or changes color. For example, the presence of an artifact may be indicated by a red light, while the absence of an artifact may be indicated by a green light or an absence of light. In some embodiments, the indicator 136 may be displayed without the concurrent display of ultrasound images. The particular nature of the indicator 136 is not critical, provided the indicator notifies the user of the presence or absence of image artifacts as a scan is being performed.

In some examples, the user interface 132 may be further configured to guide or assist a user through an ultrasound scan such that any image artifacts are removed or at least reduced in intensity. Such guidance may be generated by the neural network 128 in the form of one or more instructions 137 and may be responsive to the indicator 136 also generated by the neural network 128. For example, the user interface 132 may provide an instruction to the user in response to receiving an indicator 136 conveying the presence and/or type of an imaging artifact. The instruction may prompt the user to perform the ultrasound scan in a particular manner that ensures all image artifacts are removed from the acquired images. For example, if a reverberation artifact is detected, the user interface 132 may provide an instruction to change the viewing angle of the ultrasound transducer. For mirror images, the user interface 132 may provide an instruction to alter the imaging plane, the focal depth, and/or the pulse frequency of the transducer. Instructions may also include directional commands e.g., "Move ultrasound probe laterally," and/or technique-based commands, e.g., "Move ultrasound probe slower"; "Slow down"; "Stop"; "or "Continue." In some examples, the instructions may command the user to hold the transducer steady at one location the moment an artifact disappears, thereby allowing visualization and interpretation of the artifact-free image. Instructions may also prompt the user to make slight adjustments to the position and/or orientation of the transducer the moment an artifact is detected.

Figure 2:
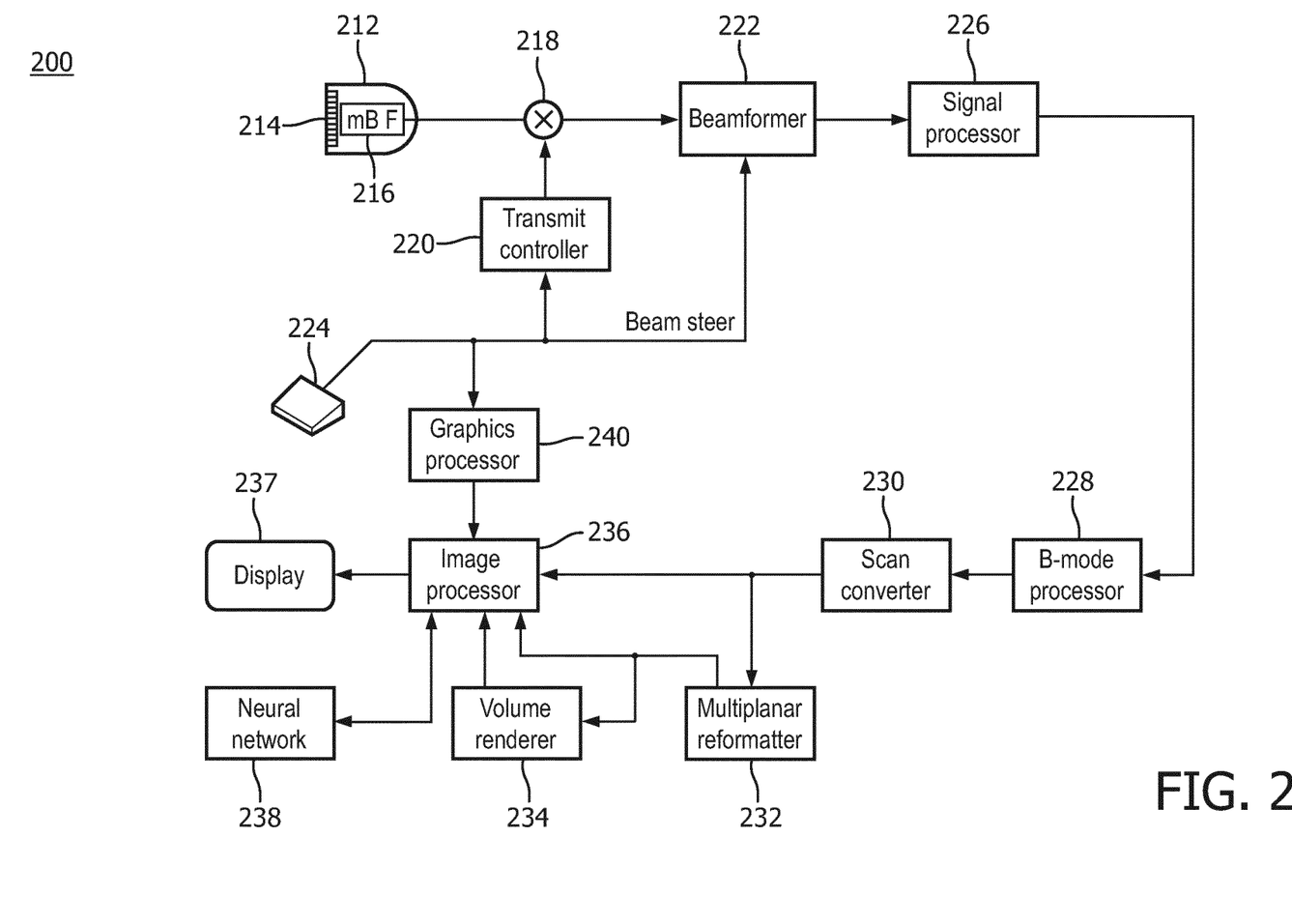
FIG. 2 is a block diagram of another ultrasound system in accordance with principles of the present disclosure.

FIG. 2 is a block diagram of another ultrasound system 200 in accordance with principles of the present inventions. One or more components shown in FIG. 2 may be included within a system configured to identify image artifacts that may appear in ultrasound image frames, provide an indication of the presence, absence and/or type thereof, provide instructions for adjusting an ultrasound transducer to remove the artifacts, and/or adjust one or more operational parameters of the ultrasound transducer automatically. For example, any of the above-described functions of the signal processor 122 may be implemented and/or controlled by one or more of the processing components shown in FIG. 2, including for example, signal processor 226, B-mode processor 228, scan converter 230, multiplanar reformatter 232, volume renderer 234 and/or image processor 236.

In the ultrasonic imaging system of FIG. 2, an ultrasound probe 212 includes a transducer array 214 for transmitting ultrasonic waves into a region containing a feature, e.g., an organ, and receiving echo information responsive to the transmitted waves. In various embodiments, the transducer array 214 may be a matrix array or a one-dimensional linear array. The transducer array may be coupled to a microbeamformer 216 in the probe 212 which may control the transmission and reception of signals by the transducer elements in the array. In the example shown, the microbeamformer 216 is coupled by the probe cable to a transmit/receive (T/R) switch 218, which switches between transmission and reception and protects the main beamformer 222 from high energy transmit signals. In some embodiments, the T/R switch 218 and other elements in the system can be included in the transducer probe rather than in a separate ultrasound system component. The transmission of ultrasonic beams from the transducer array 214 under control of the microbeamformer 216 may be directed by the transmit controller 220 coupled to the T/R switch 218 and the beamformer 222, which receives input, e.g., from the user's operation of the user interface or control panel 224. A function that may be controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals may be communicated to a signal processor 226. The signal processor 226 may process the received echo signals in various ways, such as bandpass filtering, decimation, I and Q component separation, and/or harmonic signal separation. The signal processor 226 may also perform additional signal enhancement via speckle reduction, signal compounding, and/or noise elimination. In some examples, data generated by the different processing techniques employed by the signal processor 226 may be used by a data processor and/or a neural network to identify one or more image artifacts. The processed signals may be coupled to a B-mode processor 228, which may employ amplitude detection for imaging structures in the body. The signals produced by the B-mode processor 228 may be coupled to a scan converter 230 and a multiplanar reformatter 232. The scan converter 230 may arrange the echo signals in the spatial relationship from which they were received in a desired image format. For instance, the scan converter 230 may arrange the echo signals into a two dimensional (2D) sector-shaped format. The multiplanar reformatter 232 may convert echoes which are received from points in a common plane in a volumetric region of the body into an ultrasonic image of that plane, as described in U.S. Pat. No. 6,443,896 (Detmer). In some examples, a volume renderer 234 may convert the echo signals of a 3D data set into a projected 3D image as viewed from a given reference point, e.g., as described in U.S. Pat. No. 6,530,885 (Entrekin et al.). The 2D or 3D images may be communicated from the scan converter 230, multiplanar reformatter 232, and volume renderer 234 to an image processor 236 for further enhancement, buffering and/or temporary storage for display on an image display 237. Prior to their display, a neural network 238, which may comprise a plurality of distinct neural network models, may be implemented to identify whether each image contains one or more image artifacts. In embodiments, the neural network 238 may be implemented at various processing stages, e.g., prior to the processing performed by the image processor 236, volume renderer 234, multiplanar reformatter 232, and/or scan converter 230. A graphics processor 240 can generate graphic overlays for display with the ultrasound images. These graphic overlays may contain, e.g., standard identifying information such as patient name, date and time of the image, imaging parameters, and the like, and also various outputs generated by the neural network 238, such as one or more indicators conveying the presence, absence, and/or type of image artifacts included in a particular image. Graphic overlays may also include visual instructions, e.g., text and/or symbols, for guiding a user of the system 200 through an ultrasound scan in a manner necessary to generate artifact-free images. In some examples, the graphics processor may receive input from the user interface 224, such as a typed patient name or confirmation that an instruction displayed or emitted from the interface has been acknowledged by the user of the system 200. The user interface 224 may also receive input regarding the selection of particular imaging modalities and the operating parameters included in such modalities, input prompting adjustments to the settings and/or parameters used by the system 200, input requesting additional instructions or assistance for performing an ultrasound scan, and/or input requesting that one or more ultrasound images be saved and/or transmitted to a remote receiver. The user interface may also be coupled to the multiplanar reformatter 232 for selection and control of a display of multiple multiplanar reformatted (MPR) images.

Figure 3A:
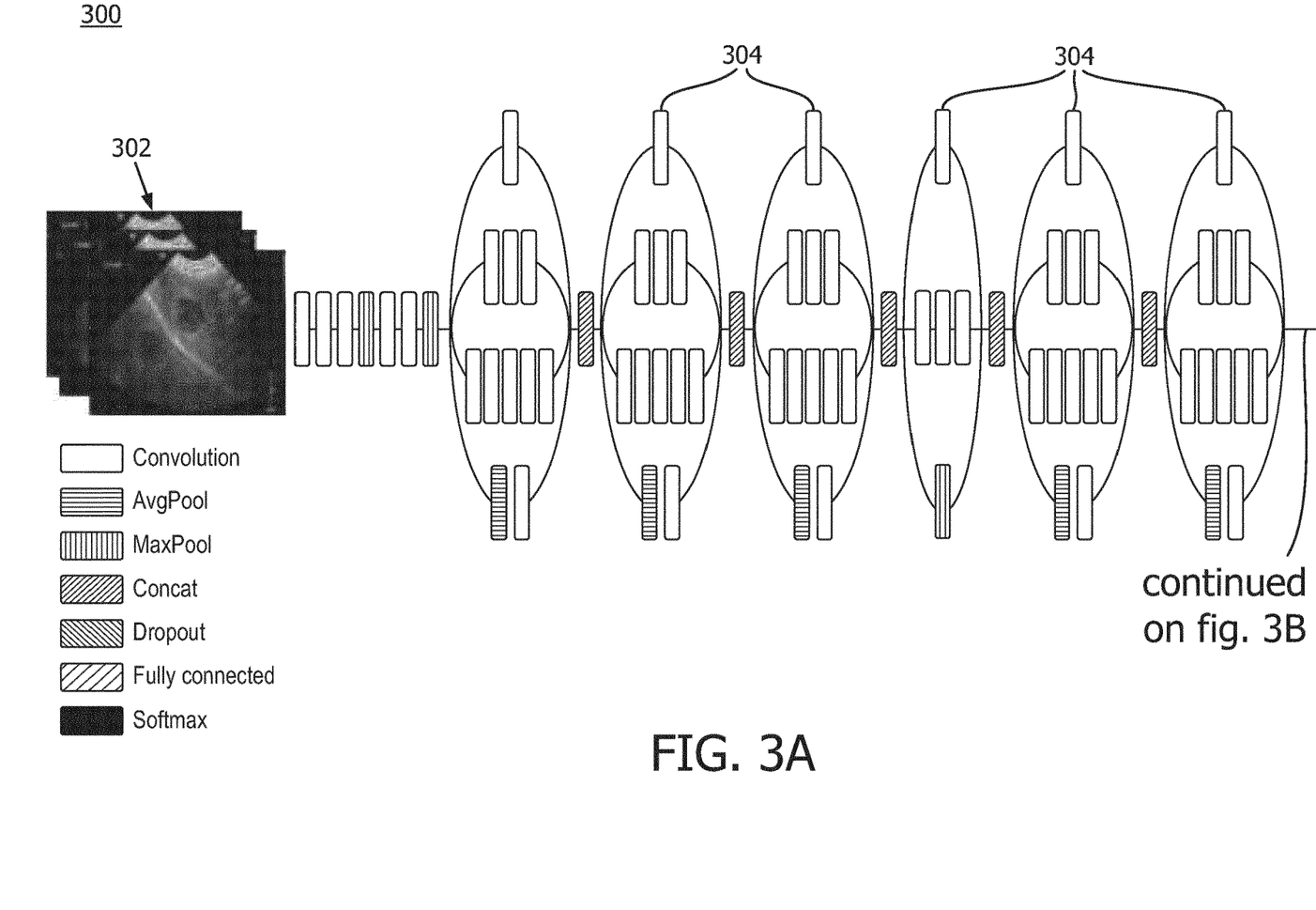
FIG. 3 is a block diagram of a neural network trained to determine a presence and type of ultrasound image artifacts in accordance with principles of the present disclosure.
Figure 3B:
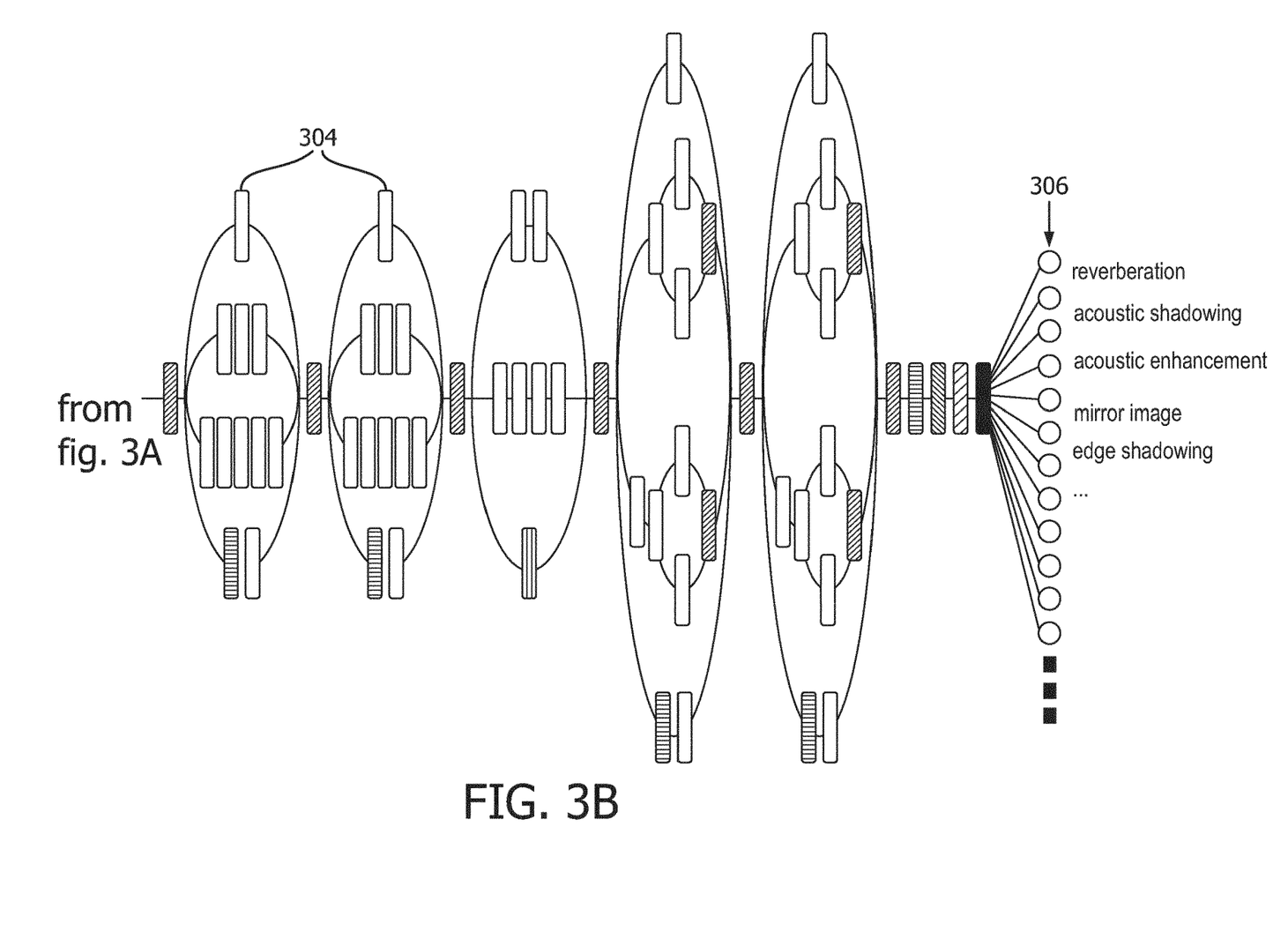

FIG. 3 is a block diagram of a neural network 300 trained to identify image artifacts in ultrasound image data according to principles of the present inventions. In the example shown, the neural network 300 is a convolutional neural network (CNN), specifically a modified version of the Inception-v3 model. Other neural networks, such as Alexnet and/or Resnet, can be used in different embodiments. The network architecture shown in FIG. 3, which is customized for detecting the presence and type of image artifacts in ultrasound image data, represents only one example of the arrangement of neural layers and sub-layers, as well as the connectivity therebetween, which may be implemented according to examples of the present invention. For example, the number of layers 304 may be greater for a neural network configured to identify a greater variety of image artifacts. Likewise, the number of layers 304 may be less for identifying a smaller number of image artifacts. In some examples, the network architecture shown in FIG. 3 may be modified by adjusting the weights and dense layers to output a multi-label classifier with a length equal to the number of different image artifact types. In various embodiments, multiple neural networks 300 may be implemented, each distinctly modified to identify image artifacts during a specific imaging modality.

The neural network 300 shown in FIG. 3 is trained to receive an input in the form of ultrasound image frames 302, which may each contain zero, one, or multiple image artifacts. Depending on the preset imaging modality selected by a user, the types of image frames 302, as well as the particular model of the neural network 300 applied, may vary. In some examples, a particular neural network model 300 may be unable to identify artifacts if provided with image frames 302 acquired via an imaging modality not associated with that particular model. The neural network 300 can be configured to receive various types of input data. For example, the network can process two-dimensional, three-dimensional, 8-bit, 16-bit, or red-blue-green channel data. In some embodiments, each layer may be trained to perform certain aspects of feature detection. For example, one or more layers 304 may be trained to recognize the edges and/or intensity levels of various features within each received image frame. One or more layers 304 may be trained to separate the image artifacts from other features having similar intensity levels. In some examples, the highest activations on the top convolutional layers can be overlaid on top of each ultrasound image frame to highlight the location of the ultrasound. This approach is advantageous over segmentation, detection or localization approaches since it does not require time-intensive expert annotation or additional machine training. In some embodiments, the training data may also include ultrasound probe adjustment instructions generated by experienced users or experts viewing the artifacts identified by the neural network. According to such embodiments, training images may be paired with removal instructions, such that the network 300 is trained to identify artifacts and methods of removing them simultaneously. The final layer may be configured to determine the type of artifact present in the image data and generate a corresponding output 306. For this reason, the final layer may be referred to as the "output layer." The output may include an indication of the presence, absence, and/or type of image artifacts present within the original input, which may include reverberation artifacts, acoustic shadowing artifacts, acoustic enhancement artifacts, mirror image artifacts, edge shadowing artifacts, or others. An instruction based on the presence and/or type of artifact(s) identified by the neural network 300 may also be output from the final layer. In some embodiments, the output may include an artifact-free image predicted by the neural network 300. In some examples, the output 306 can be visualized using fractional stride convolutional techniques. The output may be coupled to a display processor, e.g., the display processor 130 shown in FIG. 1, which may convert the output into a signal, cue, or graphic display, for example.

The neural network 300 may be implemented, at least in part, in a computer-readable medium comprising executable instructions, which when executed by a processor, such as the artifact detection engine 127, may cause the processor to perform a machine-trained algorithm to determine the presence, absence, and/or type of image artifacts contained in an image frame based on the acquired echo signals embodied therein. To train the neural network 300, training sets which include multiple instances of input arrays and output classifications may be presented to the training algorithm(s) of the neural network 300 (e.g., AlexNet training algorithm, as described by Krizhevsky, A., Sutskever, I. and Hinton, G. E. "*ImageNet Classification with Deep Convolutional Neural Networks*," NIPS 2012 or its descendants).

A neural network training algorithm associated with the neural network 300 may be presented with thousands or even millions of training data sets in order to train the neural network to identify image artifacts and provide instructions for their removal. In various examples, the number of ultrasound images used to train the neural network may range from about 50,000 to 200,000 or more. The number of images used to train the network may be increased if higher numbers of different artifacts are to be identified. The number of training images used to train the network may differ for different artifacts, and may depend on the variability in the appearance of certain artifacts. For example, features indicative of select artifacts may appear more consistently than features indicative of other artifacts. Training the neural network 300 to identify artifacts with variable features may require more training images. In some embodiments, the training may be supervised. For example, the final output 306 of the neural network 300, which may include an identified image artifact and/or instruction for removing it, may be either confirmed or rejected by an expert in ultrasound image interpretation.

Training the neural network 300 to generate predicted images that lack identified image artifacts may involve inputting ultrasound images of various features containing artifacts and associated ultrasound images of the same features obtained after an imaging adjustment has been implemented and the artifacts removed. In some examples, generating predicted artifact-free images may involve extrapolating portions of bodily features obscured by one or more artifacts. For instance, the neural network 300 may be trained to identify the edges of each artifact within a particular image frame and invert the color of the pixels defined by such edges. After this inversion, all or a portion of the inverted pixels may be modified as necessary to complete the bodily features originally obscured by the now-removed artifact(s).

Figure 4:
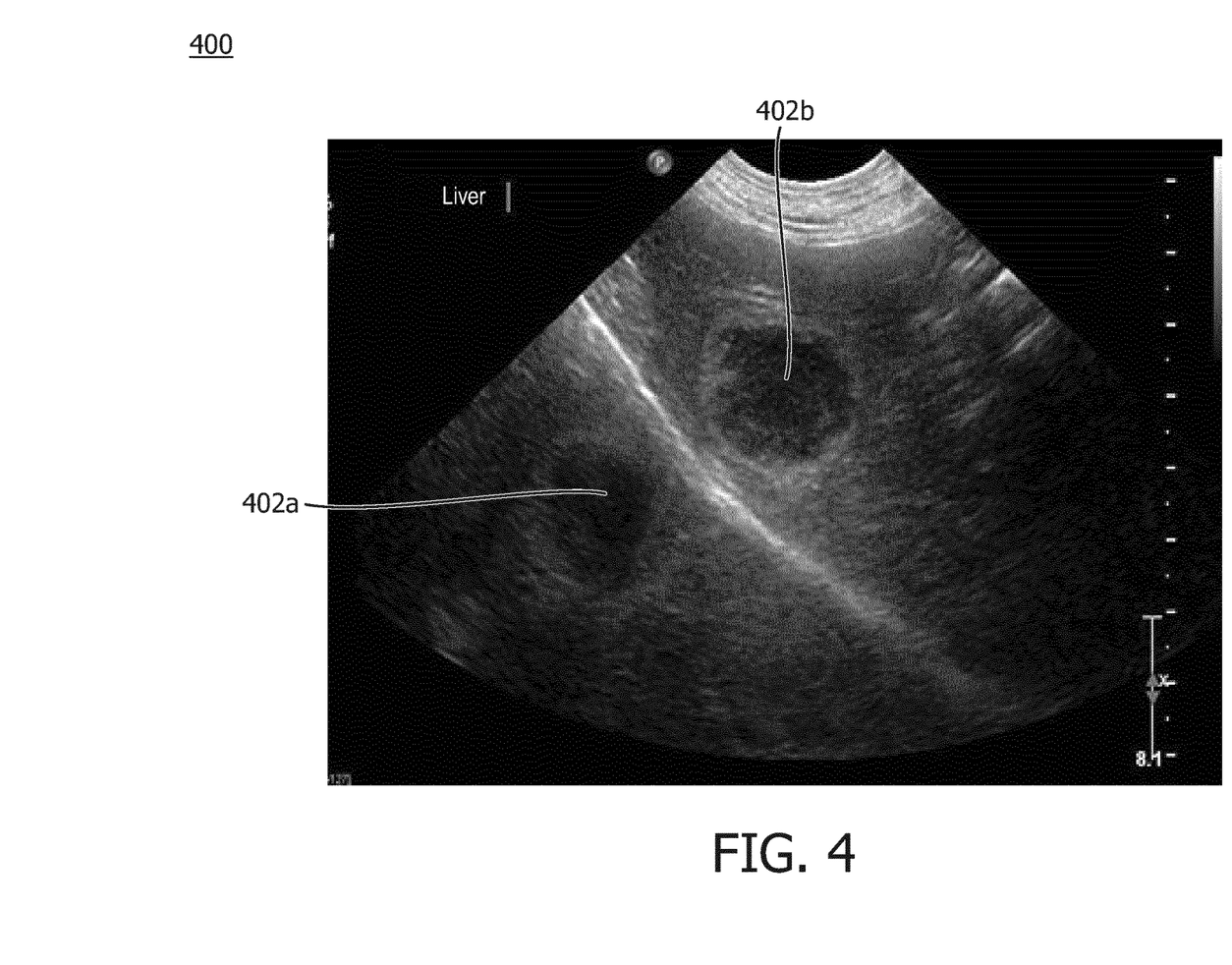
FIG. 4 is a photograph of an ultrasound image containing a mirror image artifact that has not been removed in accordance with principles of the present disclosure.

FIG. 4 is a photograph of an ultrasound image 400 containing a mirror image artifact that has not been removed. As shown, a mirror image artifact may appear as two identical features 402a and 402b arranged as reflective duplicates. Mirror image artifacts may be caused by specular reflection of an ultrasound beam at a large, smooth interface, e.g., a fluid-air interface. The systems disclosed herein can be configured to identify mirror image artifacts, such as the one shown in FIG. 4, by inputting an image frame embodying the artifact into a neural network trained to identify artifacts including mirror images. In some examples, the neural network can be trained to look specifically for mirror image artifacts based on a pre-set imaging modality selected by a user. For example, mirror image artifacts may appear frequently when imaging the bladder. Accordingly, when an imaging modality configured for imaging the bladder is selected by a user, the neural network may be trained to search specifically or preferentially for mirror image artifacts. Other features or tissue types may also be associated with specific image artifacts. For example, when imaging the pleural interface between lung tissue and the air contained within the lungs, the neural network may be configured to search specifically for reverberations, e.g., A-lines and/or B-lines. Training the neural network to look for particular artifacts when imaging particular bodily features may reduce the required processing time and increase the computing efficiency of the overall system by eliminating unnecessary processing unlikely to identify any artifacts. In some embodiments, the neural network may be trained to identify all artifacts regardless of whether a user selects a specific imaging modality. In some examples, the system may be configured to switch between a first mode of searching for a subset of image artifacts to a second mode of searching for all image artifacts used to train the neural network.

Figure 5A:
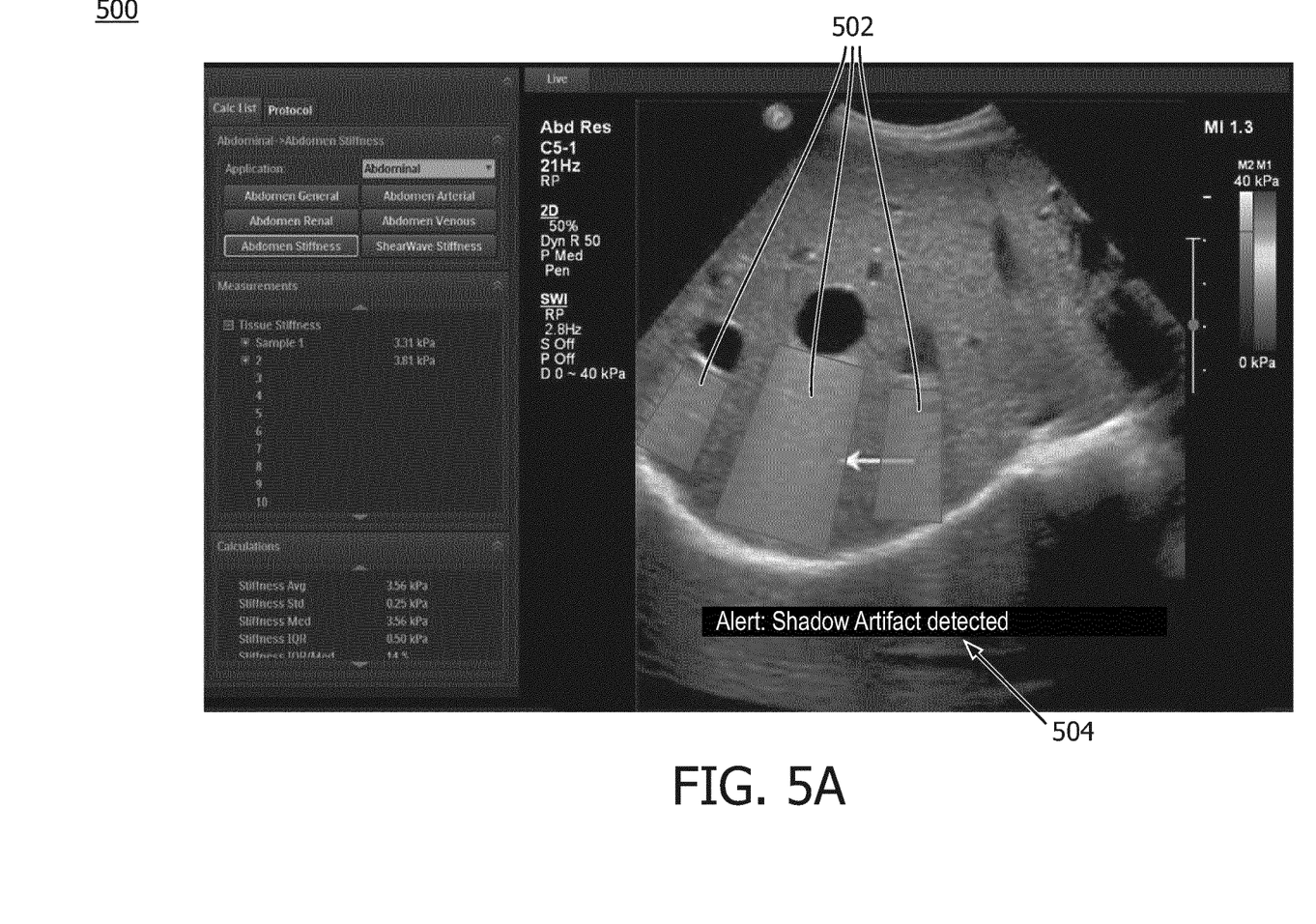
FIG. 5A is a photograph of an ultrasound image containing artifacts that have been identified and an indicator of the presence and type of such artifacts in accordance with the present disclosure.

FIG. 5A is a photograph of an ultrasound image containing artifacts that have been identified and an indicator of the presence and type of such artifacts in accordance with the present inventions. The image 500, which may be displayed on a user interface, includes three graphic overlays 502 indicating the location of the image artifacts within the image. The image 500 also includes an alert 504 indicating that shadow artifacts have been detected in the image. In other examples, an alert may not be displayed, but rather emitted as an audio cue. In addition or alternatively, the alert may be embodied in a sensory cue, such as vibration of the ultrasound transducer used to obtain the image.

Figure 5B:
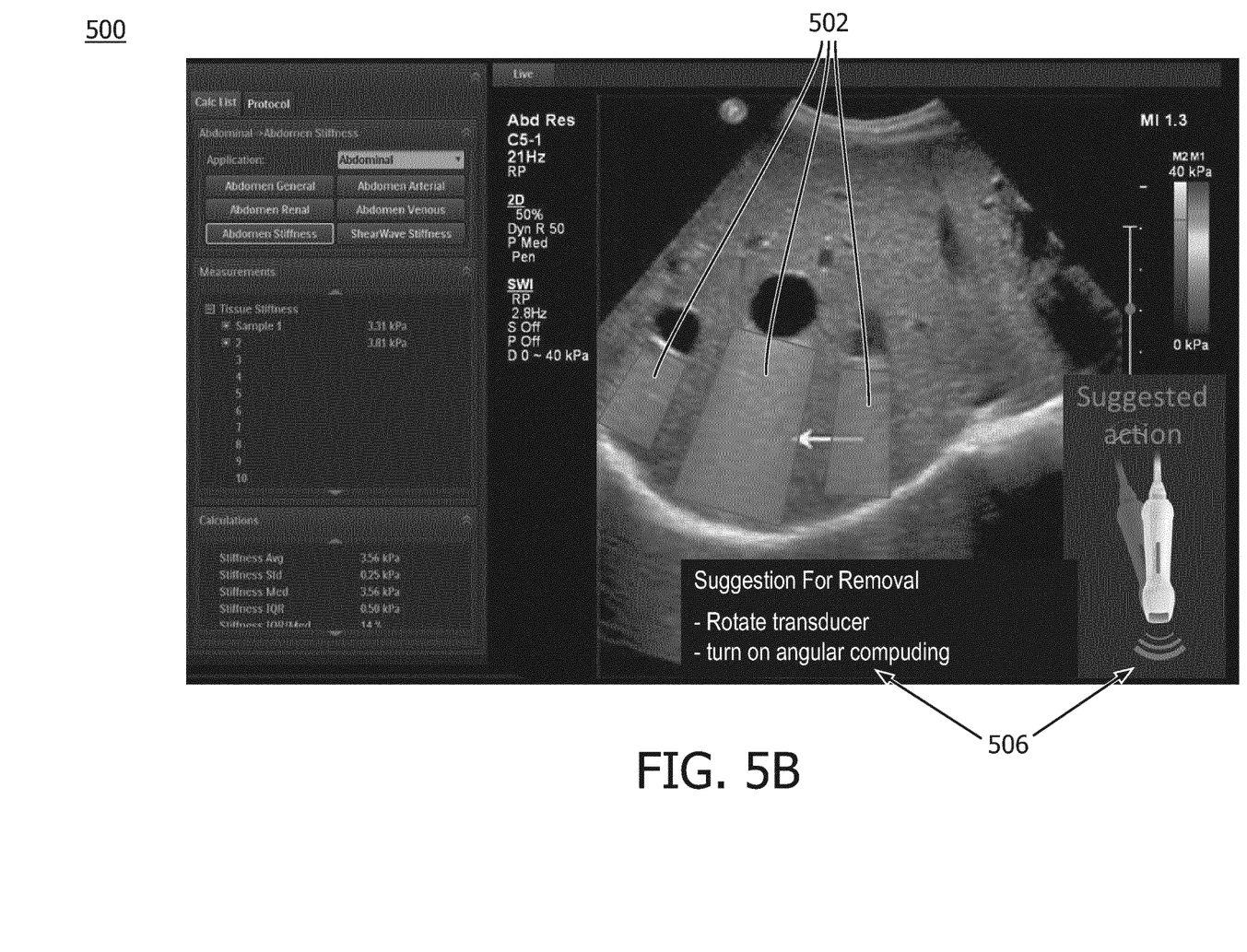
FIG. 5B is a photograph of an ultrasound image containing artifacts that have been identified and instructions for adjusting the ultrasound transducer to remove the artifacts in accordance with the present disclosure.

FIG. 5B shows the photograph 500 of in FIG. 5A, including instructions 506 for adjusting an ultrasound transducer to remove the artifacts detected in the image. As shown, example instructions may embody a "Suggestion For Removal" that may guide a user to "rotate transducer" and "turn on angular compounding." As explained herein, the instructions 506 may vary depending on the type and/or number of artifacts detected. The instruction 506 shown in FIG. 5B also includes a graphic display illustrating the maneuver that may be performed with the ultrasound transducer to remove the artifacts from the image.

In addition or alternatively, the instructions 506 may be communicated to a controller coupled with the ultrasound transducer used to acquire the image 500 as part of an operational feedback loop. According to such embodiments, the instructions 506 may be automatically converted into an adjustment of the position, orientation, and/or operational parameters of the ultrasound transducer. The adjustments may be implemented using a mechanical adjustment mechanism controlled by the controller, such that the mechanism automatically rotates the transducer and/or turns on angular compounding. The adjustments may also be implemented by modifying various imaging parameters, for example by turning on image compounding, using harmonic imaging, and/or reducing an imaging depth. The adjustments can be embodied in the instructions 506 and presented to a user for manual adjustment or automatically implemented by the system upon user approval. After following such instructions, either via the controller or manual adjustment, a new ultrasound image lacking the artifacts may be generated and/or displayed, prompting removal of the instructions 506. In some cases, adjustment of the transducer may cause one or more new artifacts to appear, causing new instructions to be displayed for their removal.

Figure 6:
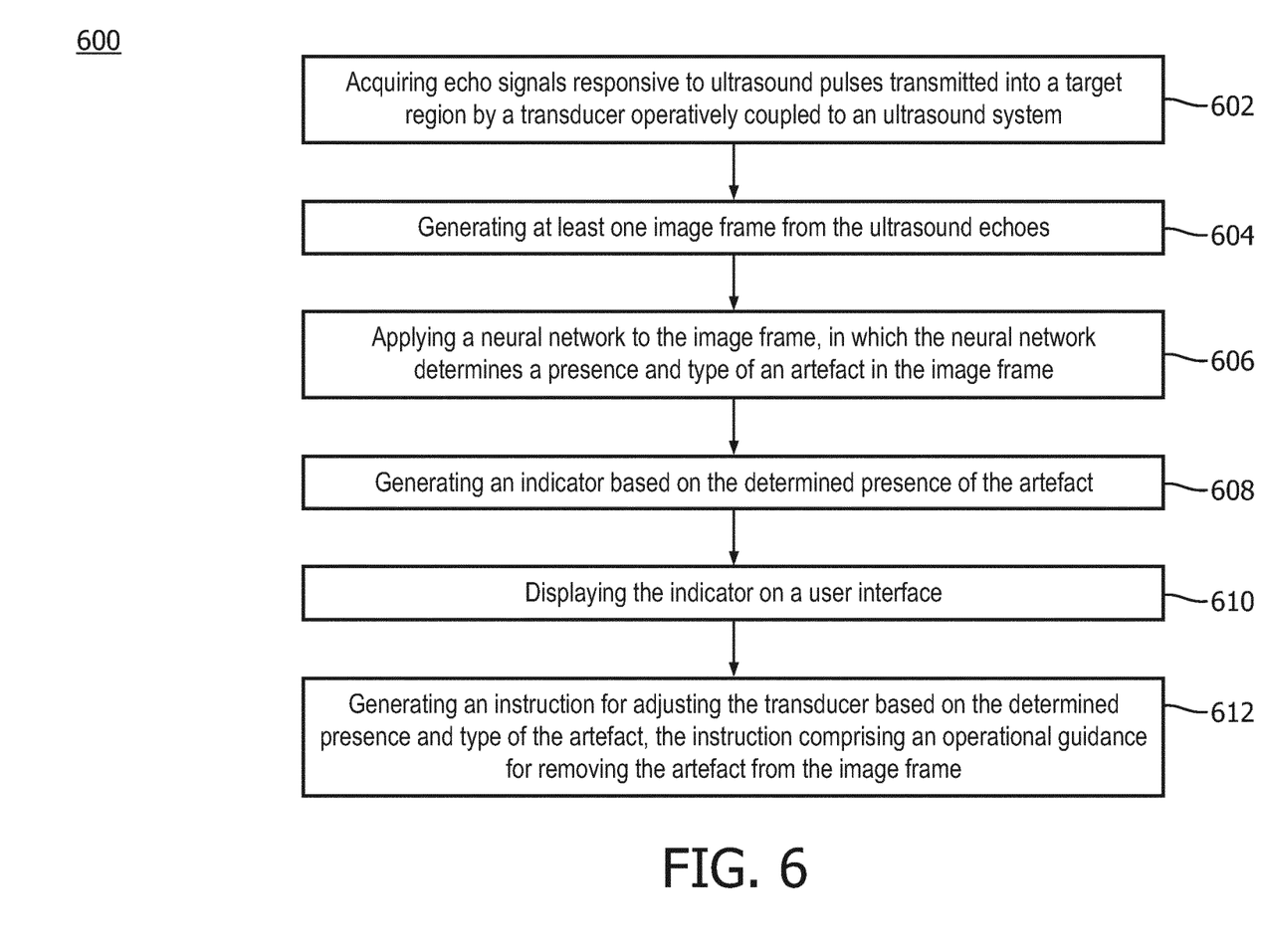
FIG. 6 is a flow diagram of a method of ultrasound imaging performed in accordance with principles of the present disclosure.

FIG. 6 is a flow diagram of a method of ultrasound imaging performed in accordance with principles of the present disclosure. The example method 600 shows the steps that may be utilized, in any sequence, by the systems and/or apparatuses described herein for identifying a presence and/or type of image artifact appearing during an ultrasound scan, which may be performed by a novice user and/or robotic ultrasound apparatus adhering to instructions generated by the system. The method 600 may be performed by an ultrasound imaging system, such as system 600, or other systems including, for example, a mobile system such as LUMIFY by Koninklijke Philips N.V. ("Philips"). Additional example systems may include SPARQ and/or EPIQ, also produced by Philips.

In the embodiment shown, the method 600 begins at block 602 by "acquiring echo signals responsive to ultrasound pulses transmitted into a target region by a transducer operatively coupled to an ultrasound system." The transducer may be manually operated by a user or implemented under the direction of a controller, which may be operating according to a pre-set imaging modality designed for imaging one or more particular features, e.g., lungs, liver, bladder, heart, etc.

At block 604, the method involves "generating at least one image frame from the ultrasound echoes." The image frame may be generated using one or more processors. In some embodiments, discrete signal processors and data processors may be included.

At block 606, the method involves "applying a neural network to the image frame, in which the neural network determines a presence and type of an artifact in the image frame." The neural network can be a convolutional neural network, such as an Inception model. The network architecture can be modified as necessary to identify a plurality of image artifacts and output an indication thereof. Training the neural network may involve inputting thousands of ultrasound images containing artifacts, as well as images free of artifacts. Training may also involve inputting instructions for removing the artifacts, and/or pairwise images with and without image artifacts.

At block 608, the method involves "generating an indicator based on the determined presence of the artifact." The indicator can be updated in substantially real time in response to movement of the transducer by a user or mechanical adjustment mechanism. The indicator can be a binary, on-or-off indicator, or the indicator can gradually change based on the number and/or type of image artifacts identified during an ultrasound scan.

At block 610, the method involves "displaying the indicator on a user interface." Displaying the indicator may involve depicting an icon conveying the presence or absence of the indicator, and/or a textual alert describing the presence and/or identity of image artifacts. In some embodiments, the indicator can be superimposed on the artifacts contained within an ultrasound image, such that the location of the artifacts is also shown. In some examples, the indicator may comprise a light that turns on or off, or changes color, based on the presence of image artifacts within an image. In some implementations, for example when the images are transmitted to an off-site specialist for analysis, the indicator may not be displayed.

At block 612, the method involves "generating an instruction for adjusting the transducer based on the determined presence and type of the artifact, the instruction comprising an operational guidance for removing the artifact from the image frame." As described herein, the instruction may be communicated to a user, who may then implement the instruction to remove the artifacts, or may be conveyed to another system component, such as a controller, configured to automatically adjust an ultrasound data acquisition unit in accordance with the instruction.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
an ultrasound transducer configured to acquire echo signals responsive to ultrasound pulses transmitted toward a target region;
one or more processors in communication with the ultrasound transducer and configured to:
generate at least one image frame from the acquired echo signals;
determine, via a neural network, a presence and type of an artifact in the at least one image frame from among different types of potential artifacts;
generate an indicator based on the determined presence of the artifact;
cause the indicator to be displayed on a user interface in communication with the processors;
generate an instruction for adjusting the ultrasound transducer based on the determined presence and type of the artifact, wherein the instruction includes a prompt to modify an operating parameter of the ultrasound transducer intended to remove the artifact from the at least one image frame, and wherein the operating parameter comprises a position, an orientation, a focal depth, a beam angle, an imaging modality, or a frequency of the ultrasound transducer; and
wherein the one or more processors are further configured to prepare the at least one image frame for input into the neural network by creating triplicate replications of the at least one image frame such that at least one of a plurality of neural network models can be utilized to determine the presence, an absence, and/or type of an artifact in the at least one image frame; and
wherein the triplicate replications of the at least one image frame includes: (i) a high-signal, low-dynamic range image; (ii) a low-signal, low-dynamic range image; and (iii) a compressed high-dynamic range image with an adaptive histogram equalization.

2. The ultrasound imaging system of claim 1, wherein the one or more processors are further configured to transmit the instruction to a controller communicatively coupled with the ultrasound transducer.

3. The ultrasound imaging system of claim 2, wherein the controller is configured to adjust the ultrasound transducer by modifying at least one operating parameter thereof based on the instruction received from the one or more processors.

4. The ultrasound imaging system of claim 3, wherein the ultrasound transducer is physically coupled with a robotic arm configured to move the ultrasound transducer.

5. The ultrasound imaging system of claim 1, wherein the one or more processors are further configured to generate and cause to be displayed an ultrasound image from the least one image frame on the user interface.

6. The ultrasound imaging system of claim 5, wherein the indicator comprises a graphic overlay superimposed on the ultrasound image displayed on the user interface.

7. The ultrasound imaging system of claim 1, wherein each of at least one of the plurality of neural network models associated with one of a plurality of preset imaging modalities is selectable by a user.

8. The ultrasound imaging system of claim 7, wherein each of the preset imaging modalities is configured to cause the ultrasound transducer to acquire echo signals from a distinct target region by implementing a set of operating parameters specific to the distinct target region.

9. The ultrasound imaging system of claim 1, wherein the one or more processors are further configured to generate and cause to be displayed a predicted artifact-free ultrasound image.

10. A method of ultrasound imaging, the method comprising:
    acquiring echo signals responsive to ultrasound pulses transmitted into a target region by a transducer operatively coupled to an ultrasound system;
    generating at least one image frame from the acquired echo signals;
    determining, via a neural network, a presence and type of an artifact in the at least one image frame from among different types of potential artifacts;
    generating an indicator based on the determined presence of the artifact;
    displaying the indicator on a user interface;
    generating an instruction for adjusting the transducer based on the determined presence and type of the artifact, the instruction comprising an operational guidance for removing the artifact from the least one image frame by modifying an operational parameter of the ultrasound transducer, wherein the operational parameter comprises a position, an orientation, a focal depth, a beam angle, an imaging modality, or a frequency of the ultrasound transducer; and
    wherein the one or more processors are further configured to prepare the at least one image frame for input into the neural network by creating triplicate replications of the at least one image frame such that at least one of the plurality of neural network models can be utilized to determine a presence, absence, and/or type of an artifact in the at least one image frame; and
    wherein the triplicate replications of the at least one image frame includes: (i) a high-signal, low-dynamic range image; (ii) a low-signal, low-dynamic range image; and (iii) a compressed high-dynamic range image with an adaptive histogram equalization.

11. The method of claim 10, further comprising selecting an imaging modality for acquiring the echo signals, the imaging modality comprising operational parameters specific to the target region.

12. The method of claim 10, further comprising transmitting the instruction to a controller communicatively coupled with the ultrasound transducer.

13. The method of claim 12, further comprising modifying an operating parameter of the transducer based on the instruction.

14. The method of claim 10, further comprising displaying the instruction on the user interface.

15. The method of claim 10, further comprising training the neural network using ultrasound image frames containing a plurality of different artifacts and user instructions for adjusting the ultrasound transducer based on the plurality of different artifacts.

16. The method of claim 10, further comprising generating a predicted ultrasound image without the artifact.

17. A non-transitory computer-readable medium comprising executable instructions, which when executed cause a processor of a medical imaging system to perform the method of claim 10.

18. An ultrasound imaging system comprising:
    an ultrasound transducer configured to acquire echo signals responsive to ultrasound pulses transmitted toward a target region;
    one or more processors in communication with the ultrasound transducer and configured to:
        generate at least one image frame from the acquired echo signals;
        prepare the at least one image frame for input into a neural network, wherein the neural network is configured to determine a presence and type of an artifact in the at least one image frame from among different types of potential artifacts
        input the prepared at least one image frame from the acquired echo signals to the neural network;
        receive, from the neural network, an output comprising a determination of a presence, absence, and/or type of an artifact in the at least one image frame;
        generate an indicator based on the determined presence, absence, and/or type of the artifact in the at least one image frame;
        cause the indicator to be displayed on a user interface in communication with the one or more processors;
        generate an instruction for adjusting the ultrasound transducer based on the determined presence, absence, and/or type of the artifact, wherein the instruction includes a prompt to modify an operating parameter of the ultrasound transducer intended to remove the artifact from the at least one image frame, and wherein the operating parameter comprises a position, an orientation, a focal depth, a beam angle, an imaging modality, or a frequency of the ultrasound transducer; and
    wherein the one or more processors are further configured to prepare the at least one image frame for input into the neural network by creating triplicate replications of the at least one image frame such that at least one neural network model can be utilized to determine a presence, absence, and/or type of an artifact in the at least one image frame; and wherein the triplicate replications of the at least one image frame includes: (i) a high-signal, low-dynamic range image; (ii) a low-signal, low-dynamic range image; and (iii) a compressed high-dynamic range image with an adaptive histogram equalization.

\* \* \* \* \*